United States Patent [19]
Wing et al.

[11] 4,001,593
[45] Jan. 4, 1977

[54] AXIAL TOMOGRAPHIC SCANNER HAVING MEANS FOR SUPPORTING X-RAY SOURCE CABLES

[75] Inventors: James C. Wing, Los Altos; Jack V. White, Los Gatos, both of Calif.

[73] Assignee: Syntex (U.S.A.) Inc., Palo Alto, Calif.

[22] Filed: Oct. 20, 1975

[21] Appl. No.: 623,848

[52] U.S. Cl. .................. 250/522; 174/69; 191/12 R; 250/422
[51] Int. Cl.² .............. A47B 3/10; A45F 3/00; H05G 1/10
[58] Field of Search .......... 250/422, 522, 526; 191/12 R; 174/69

[56] References Cited
UNITED STATES PATENTS

| | | | |
|---|---|---|---|
| 2,959,634 | 11/1960 | Lyon | 174/69 |
| 3,541,334 | 11/1970 | Sobolewski | 174/69 |
| 3,551,612 | 12/1970 | Guentner | 250/522 X |

*Primary Examiner*—Alfred E. Smith
*Assistant Examiner*—T. N. Grigsby
*Attorney, Agent, or Firm*—Joseph I. Hirsch; William B. Walker

[57] ABSTRACT

An axial tomographic scanner having means for supporting a plurality of cables leading to the X-ray source including a yoke upon which the X-ray source is mounted, first bracket means mounted on the yoke adjacent the X-ray source for restraining cable movement, second bracket means mounted on the yoke remote from the X-ray source for restraining cable movement, and means disposed between the first and second bracket means for maintaining the cables passing therethrough in a gradual arc while preventing undue flexing of the cables and undesirable movement of the cables into interfering position with other components of the axial tomographic scanner. The cable maintaining means disposed between the first and second bracket means comprises a pair of flexible elongated bands extending on opposite sides of the cables from the first bracket means to the second bracket means and a cable guide, one end of which securely engages one of the bands while the other end surrounds a portion of the other band and restrains lateral movement thereof, the side portions of the cable guide serving to prevent transverse movement of the cables passing therethrough so as to maintain the pair of bands and those portions of the cables between the first and second bracket means in a generally planar, arcuate configuration during all rotational movements of the yoke and translational movements, if any, of the X-ray source.

10 Claims, 5 Drawing Figures

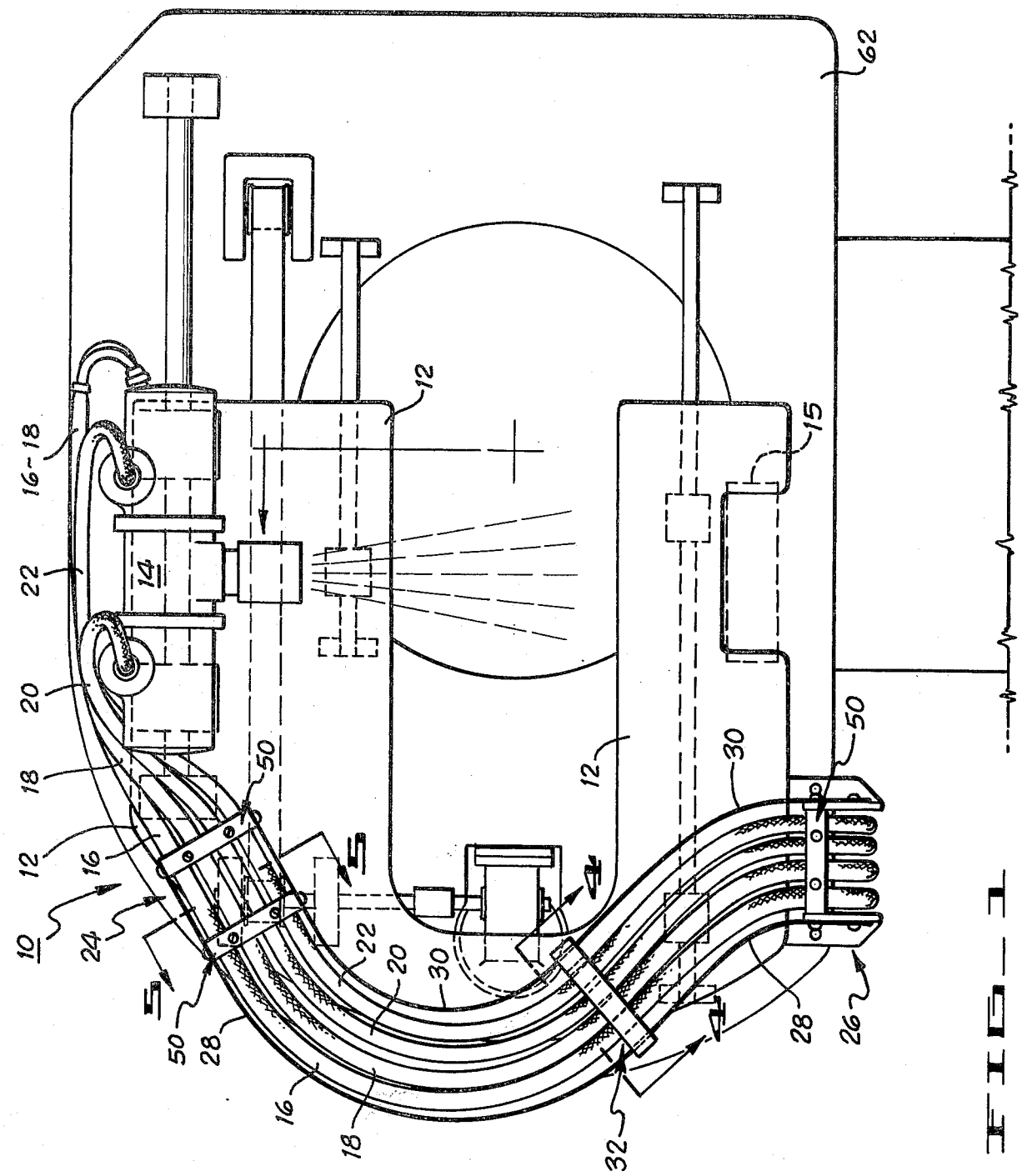
FIG—1

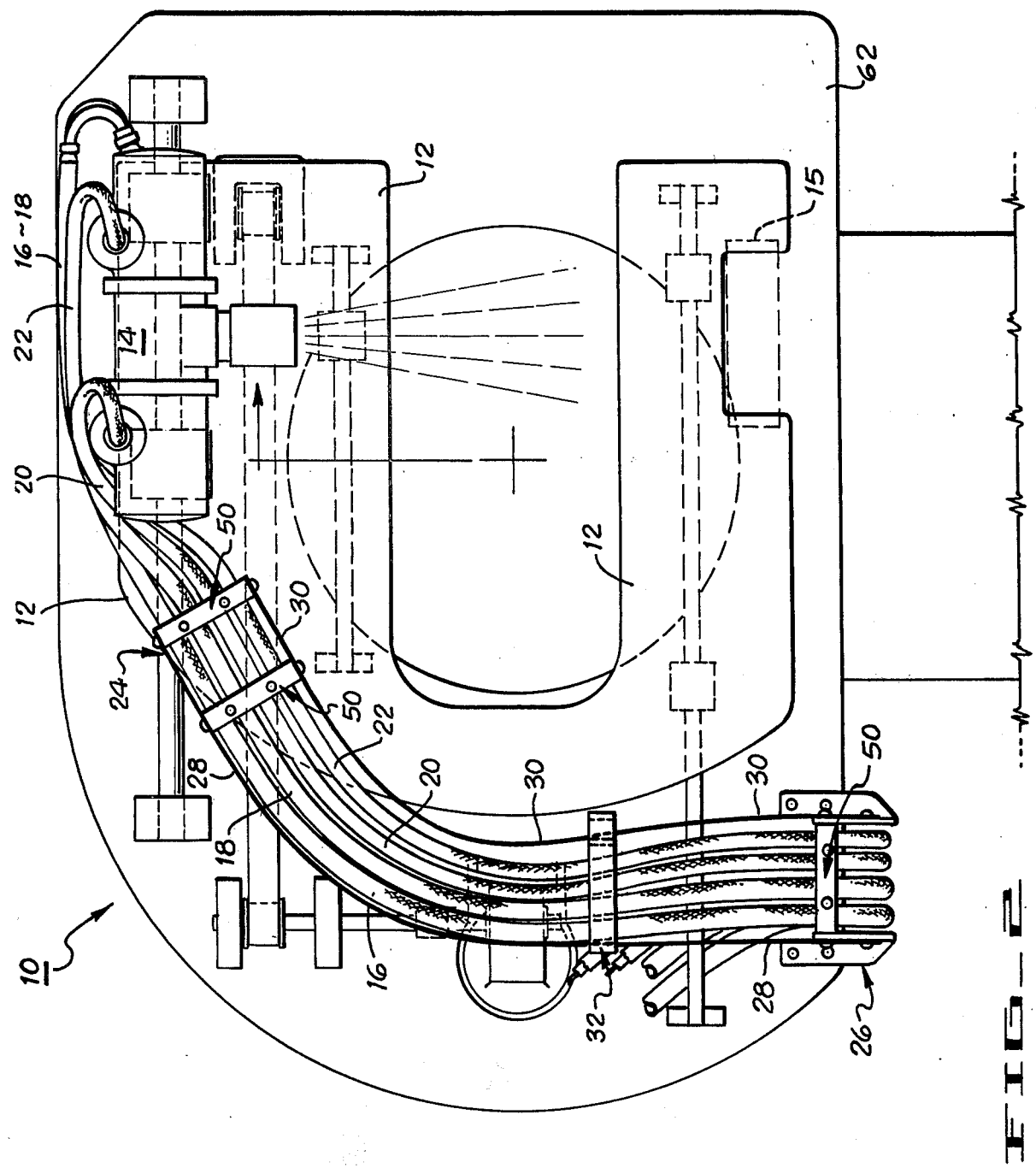

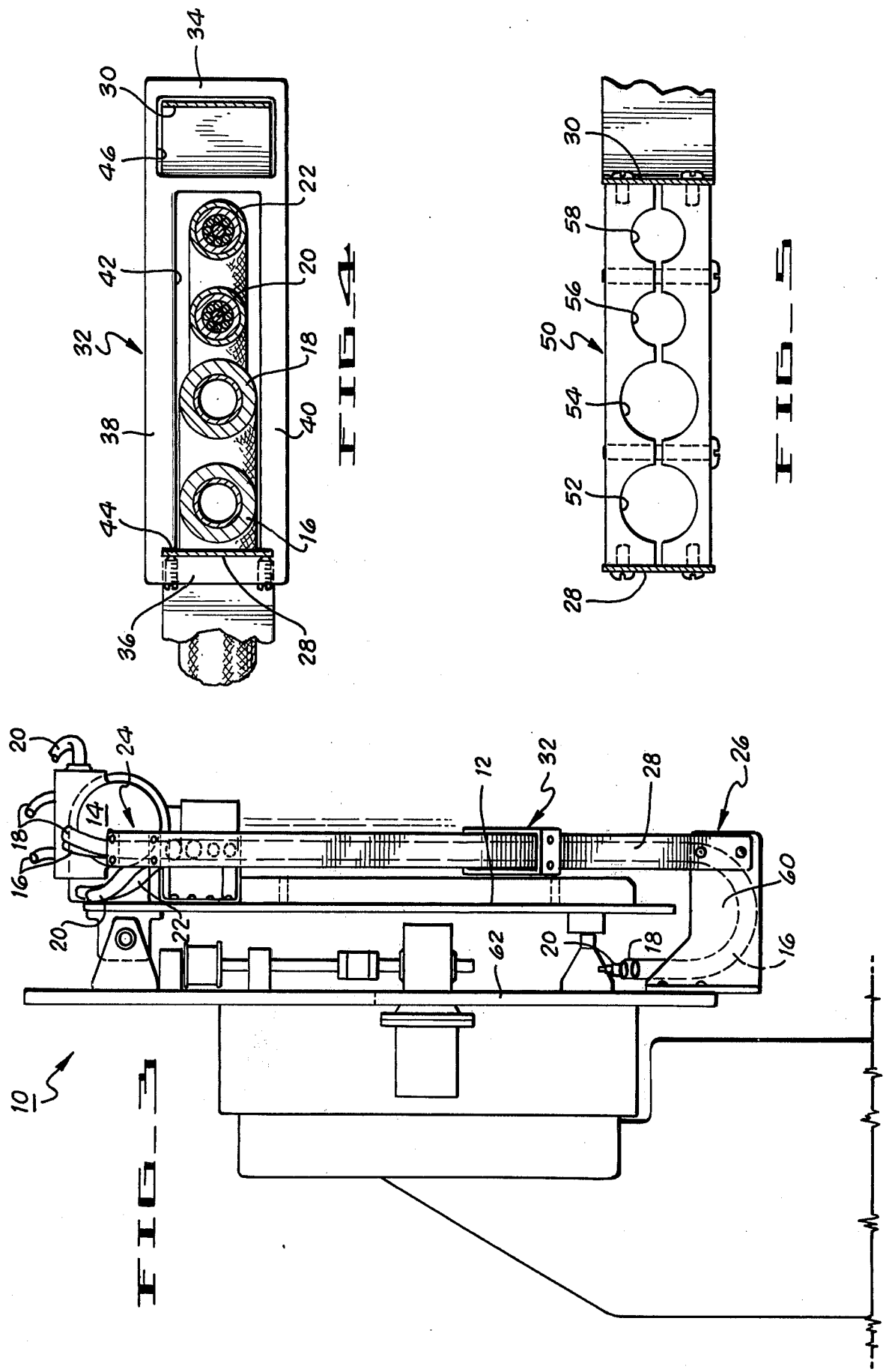

AXIAL TOMOGRAPHIC SCANNER HAVING MEANS FOR SUPPORTING X-RAY SOURCE CABLES

FIELD OF THE INVENTION

This invention relates to means for supporting a plurality of flexible cables so as to prevent undue interference with other components of an axial tomographic scanner. More particularly, this invention relates to means for supporting a plurality of cables leading to an X-ray source whereby undue flexing of the cables and undesirable movement of the cables into interferring position with other components of the axial tomographic scanner is prevented.

OBJECTS OF THE INVENTION

It is the primary object of the present invention to provide novel means for securing a plurality of flexible cables to an axial tomographic scanner.

It is a further object of the present invention to provide novel means for securing a plurality of flexible cables to the yoke of an axial tomographic scanner in a manner which prevents undue flexing of the cables and undesirable movement of the cables into interferring position with other components of the axial tomographic scanner.

It is a further object of the present invention to provide an axial tomographic scanner incorporating the novel flexible cable supporting means of the present invention.

Yet a still further object of the present invention is to provide an axial tomographic scanner having an X-ray source and means for supporting a plurality of cables leading to the X-ray source is such a manner that undue flexing of the cables and undesirable movement of the cables into interferring position with other components of the axial tomographic scanner is prevented.

These and still further objects, features and advantages of the present invention will become apparent upon consideration of the following detailed disclosure.

BRIEF SUMMARY OF THE INVENTION

The above and still further objects, features and advantages of the present invention are achieved, in accordance therewith, by providing an axial tomographic scanner having means for supporting a plurality of cables leading to an X-ray source mounted thereon, the scanner including a yoke upon which the X-ray source is mounted, first bracket means mounted on the yoke adjacent the X-ray source for restraining cable movement, second bracket means mounted on the yoke remote from the X-ray source for restraining cable movement, and means disposed between the first and second means for maintaining the cables passing therethrough in a gradual arc between the first and second bracket means while preventing undue flexing of the cables and undesirable movement of the cables into interferring position with other components (i.e., the collimators, the path of the X-ray beam, etc.) of the axial tomographic scanner. The cable maintaining means disposed between the first and second bracket means comprises a pair of flexible elongated bands on opposite sides of the cable from the first bracket means to the second bracket means and a cable guide, one end of which securely engages one of the bands while the other end surrounds a portion of the other band and restrains lateral movement thereof. The side portions of the cable guide prevent transverse movement of the cables passing therethrough so as to maintain the pair of bands and those portions of the cables between the first and second bracket means in a generally planar, arcuate configuration during all rotational movements of the yoke and translational movements, if any, of the X-ray source.

The axial tomographic scanner, in one configuration thereof, has a source of X-rays or $\gamma$-rays adapted to transmit one or more beams of radiation through a planar slice of the object to be examined, detector means to detect the transmitted beam(s) after it has passed through the object, and means to sequentially translate and rotate the source and detector means about the object during the radiographic examination. Such a scanner is shown, for example, by U.S. Pat. No. 3,778,614. In a different configuration, as shown by co-pending application Ser. No. 528,026, filed Nov. 29, 1974, in the name of Douglas Boyd et al, a fan-shaped beam of penetrating radiation is directed through the slice of the object to be analyzed to a radiation-sensitive detector for deriving a set of data corresponding to the transmission or absorption of the penetrating radiation by the object along a plurality of divergent lines extending from the source to the detector. A number of sets of such data are obtained for different angles of rotation of the fan-shaped beam relative to the center of the slice being analyzed. The principal difference between this configuration, and the preceeding configuration, is that in this configuration there is no lateral translation of the source and the detector, rather the source and the detector need only be rotated about the object undergoing examination to provide sufficient sets of data to permit the necessary reconstruction of the particular slice being examined. The cable supporting means of the present invention can be utilized in conjunction with either of the aforesaid configurations, other axial tomographic configurations which may differ from the above configuration, or other X-ray or $\gamma$-ray apparatus and configurations which require means for supporting a plurality of flexible cables in a manner which permits all desired movements without undue flexing of the cables or undesirable movement of the cables into interferring position with other components of the apparatus. U.S. Pat. No. 3,778,614 and co-pending application Ser. No. 528,026, filed Nov. 29, 1974, are incorporated herein by reference to the extent necessary to complete, or render fully understandable, the disclosure of this application.

The support means per se comprises first bracket means mounted on the yoke of the axial tomographic scanner adjacent the x-ray source for restraining cable movement, second bracket means mounted on the yoke remote from the X-ray source for restraining cable movements, and means disposed between the first and second bracket means for maintaining the cables passing therethrough in a gradual arc while preventing undue flexing of the cables and undesirable movement of the cables into interferring position with other components of the axial tomographic scanner. Specifically, the cable maintaining means disposed between the first and second bracket means includes a pair of flexible elongated band secured at their ends to the first and second bracket means. The bands are positioned on opposite sides of those portions of the plurality of cables extending between the first and second bracket means, and, in combination with those portions of the flexible cables, generally define a thick, planar arcuate configuration. The cable maintaining means further includes a substantially rectangular cable guide, one lateral end of which has a notch which securely engages one of the bands, but substantially prevents other undesirable motion of the band and/or cable guide. The plurality of flexible cables pass through a substantially rectangular opening in the majority of the remaining portion of the cable guide; however, a cross member serves to define a separate rectangular opening through which the other band passes. This separate rectangular opening restrains transverse movement of the band while permitting sufficient movement of the cable guide so as to prevent and/or restrain undesirable movement of those portions of the cables extending between the first and second bracket member. Thus, during all rotational movements of the yoke upon which the X-ray source is mounted and translational movement, if any, of the X-ray source upon translation means therefor (if any), the cable supporting means of this invention prevents undue flexing of the plurality of flexible cables which would shorten the useful life thereof and, in addition, prevents lateral movement of the cables or other movement of the cables which would interfer with the intended function of the other components of the axial tomographic scanner.

BRIEF DESCRIPTION OF THE DRAWINGS

The features and advantages of the present invention will become more apparent from the following detailed description, taken together with the accompanying drawings wherein:

FIG. 1 is a front elevational view of an axial tomographic scanner showing the cable maintaining means of the present invention when the X-ray source is at the extreme left-hand lateral position;

FIG. 2 is a front elevational view of the axial tomographic scanner of FIG. 1 showing the cable maintaining means of the present invention when the X-ray source is at the extreme right-hand position;

FIG. 3 is a side view of the axial tomographic scanner and cable maintaining means of FIG. 1;

FIG. 4 is a partial cross-sectional view taken along line 4—4 of FIG. 1 showing the cable guide of the present invention; and FIG. 5 is a partial cross-sectional view taken along line 5—5 of FIG. 1 showing the clamp for mounting the plurality of cables to the yoke of the axial tomographic scanner.

Referring to FIGS. 1-3, there is shown an axial tomographic scanner 10 having a yoke 12 upon which there is mounted an X-ray source 14 and detector 15. A pair of cables or conduits 16 and 18 for flowing cooling fluid to and from X-ray source 14 and a pair of electrical cables 20 and 22 connected to X-ray source 14 are shown. First bracket means 24 is mounted on yoke 12 adjacent X-ray source 14. A second bracket means is also mounted on yoke 12 remote from X-ray source 14, generally about 130° or so around the yoke from the X-ray source. The cables are also fixedly secured to the rear side of yoke 12 by further bracket means (not shown) and from there are strung in loose fashion to the respective components at the other ends thereof so as to permit complete rotation of scanner 10 without need for bulky, complex equipment to achieve this result. First and second bracket means 24 and 26 by themselves are considered insufficient to support the plurality of cables 16, 18 20 and 22 (along the arc between the brackets) since during the rotational movements of yoke 12 and the translational movements, if any, of X-ray source 14, the cables would be subjected to undue flexing which would shorten the useful life thereof (any failure thereof during actual operation of the equipment could, in fact, be highly disadvantageous) and could potentially be flexed into interferring position or contact with other components of the axial tomographic scanner (e.g., the collimators, the path of the X-ray beam from the X-ray source to the detector means, etc.). Thus, the present invention provides further cable restraining means for assuring desirable positioning of the flexible cables during all rotational movements of the yoke and translational movements, if any, of the X-ray source. Specifically, flexible bands 28 and 30 are connected to opposite, lateral ends of brackets 24 and 26 whereby such bands prevent movement of the flexible cables out of the general arc which the cables normally assume between brackets 24 and 26. In addition, cable guide 32, described in greater detail below, restrains cable movement in the other (i.e., transverse) direction whereby the bands and those portions of the flexible cables extending between brackets 24 and 26 are maintained in a generally thick, planar configuration which achieves the purposes of this invention.

Referring to FIG. 4, cable guide 32 is shown in greater detail. Specifically, cable guide 32 is of generally rectangular configuration having lateral end walls 34 and 36 and side walls 38 and 40. The plurality of flexible cables 16, 18, 20 and 22 are adapted to pass through elongated rectangular opening 42 which terminates, at the end adjacent lateral side wall 36 in a notch 44. Flexible band 28 passes through notch 44 and is securely fastened thereto by means of a plurality of set screws 45. At the end of guide number 32 adjacent lateral side wall 34 there is a second rectangular opening 46 through which flexible band 30 extends. If desired, band 30 could be fixedly secured to guide 32 and band 28 adapted for greater freedom of movement during rotation of yoke 12 and translation, if any, of X-ray source 14. As set forth above, bands 28 and 30 maintain the generally thick, planar configuration of the flexible cables in the lateral direction while side walls 38 and 40 of cable guide 32 maintain the generally thick, planar configuration in the transverse direction. Notwithstanding these particular constraints on cable movement, the overall configuration of the cable supporting means of the present invention permits the necessary movement of the flexible cables while, at the same time, maintaining the freedom from interference with other components on the axial tomographic scanner.

Referring to FIG. 5, there is shown cable holding elements 50 forming a part of bracket means 24 and 26. Bracket 50 includes circular holes 52 and 54 for thicker coolant cables 16 and 18, respectively, and relatively smaller holes 56 and 58 for relatively smaller electrical cables 20 and 22. As shown, a single cable holding element 50 is secured by support 60 to backing plate 62 while two cable holding elements 50 are utilized in conjunction with first bracket means 24.

Cables 16, 18, 20 and 22 also extend from bracket means 26 to the terminals therefor (not shown) at the extreme end thereof remote from X-ray source 14. The cables are connected to a cable reel (not shown) which moves up and down in response to the tension applied to the cables by virtue of the movement of the scanning mechanism during the scanning cycle(s). This connection of the cables to the cable reel further simplifies the mechanism for supporting the cables in a manner which extends the useful life thereof.

As indicated above, the cable support means of this invention is particularly adapted for use with an axial tomographic scanner where the cables leading to and from the X-ray (or γ-ray) source are subjected to a severe "duty-cycle" (i.e., where the cables are subjected to extensive flexing movements caused by an extensive number of high velocity traverses of the source laterally of the object and/or an extensive number of highly arcuate rotational movements about the object). This severe duty-cycle necessitates means which prevent undue flexing of the cables so as not to shorten the useful life thereof, a need which is satisfied by the support means described herein.

While the invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. Means for supporting a plurality of flexible cables on a moveable yoke; said means comprising first bracket means adapted to be mounted at a first position on the yoke, second bracket means adapted to be mounted on the yoke at a second position romote from the first position, and means disposed between said first and second bracket means for maintaining flexible cables passing therethrough in a gradual arc while preventing undue flexing of the flexible cables, said means disposed between said first and second bracket means comprising a pair of flexible elongated bands adapted to extend on opposite lateral sides of flexible cables extending from said first bracket means to said second bracket means and a cable guide, one lateral end of said guide securely engaging one of said bands while the other end of said guide surrounds a portion of the other band and restrains lateral movement thereof, the side portions of said cable guide serving to prevent transverse movement of flexible cables passing therebetween and the surrounded band, whereby said bands and those portions of the flexible cables extending between said first and second bracket means are maintained in a generally thick planar, arcuate configuration.

2. The support means of claim 1 wherein said first and said second bracket means are rigidly mounted on said yoke.

3. The support means of claim 1 wherein said cable guide is of substantially rectangular configuration having a first substantially rectangular opening adapted to receive the plurality of flexible cables, said substantially rectangular opening terminating in a notch adapted to receive one of said bands, and a second substantially rectangular opening adapted to receive the other of said bands.

4. The support means of claim 3 wherein said cable guide further includes means for securely fastening to said cable guide said band which is received within said notch.

5. An axial tomographic scanner comprising axial tomographic means for collecting a plurality of sets of data corresponding to the transmission or absorption of a plurality of beams of penetrating radiation through a planar slice of an object being analyzed including means to locate an object to be analyzed, source and detector means mounted on a yoke for directing one or more beams of penetrating radiation through the object from said source to said detector means, said source having a plurality of flexible cables connected thereto, means to rotate said yoke and said source and said detector means mounted thereon about the object whereby a plurality of sets of data corresponding to the transmission or absorption of the object of the plurality of beams of penetrating radiation are collected, and means for supporting a plurality of flexible cables leading to said source, said cable supporting means comprising first bracket means mounted on said yoke adjacent said source for restraining cable movement, second bracket means mounted on said yoke remote from said source for restraining cable movement, and means disposed between said first and said second bracket means for maintaining said cables passing therethrough in a gradual arc while preventing undue flexing of said cables, said cable maintaining means comprising a pair of flexible elongated bands extending on opposite lateral sides of those portions of said flexible cables extending from said first bracket means to said second bracket means and a cable guide, one lateral end of said cable guide securely engaging one of said bands and the other lateral end of said cable guide surrounding a portion of said other band whereby lateral movement of said bands is restrained, said cable guide having transverse side portions connecting said lateral ends which serve to prevent transverse movement of said cables and said bands passing therebetween, whereby said pair of bands and those portions of said cables extending between said first and said second bracket means are maintained in a generally thick planar, arcuate configuration during all rotational movements of said yoke and translational movements, if any, of said source.

6. The scanner of claim 5 wherein said source directs a divergent beam of penetrating radiation through the object and said means for rotating said yoke effects relative angular displacement between the divergent beam of penetrating radiation and the object in a manner which is substantially free of relative lateral translation therebetween.

7. The scanner of claim 5 wherein said source directs a divergent beam of penetrating radiation through the object and said means for rotating said yoke about the object further includes means for translating said source laterally across the object between successive rotations of said yoke by said rotation means.

8. The scanner of claim 5 wherein said first and said second bracket means are rigidly mounted on said yoke.

9. The scanner of claim 5 wherein said cable guide is of substantially rectangular configuration having a first substantially rectangular opening for receiving said plurality of flexible cables, said substantially rectangular opening terminating in a notch for receiving one of said bands, and a second substantially rectangular opening for receiving the other of said bands.

10. The scanner of claim 9 wherein said cable guide further includes means for securely fastening to said guide said band which is received within said notch.

* * * * *